United States Patent [19]

Wartman

[11] 4,019,505
[45] Apr. 26, 1977

[54] METHOD OF FORMING AN ORTHOPEDIC CAST

[75] Inventor: Lloyd H. Wartman, Norwalk, Conn.

[73] Assignee: Norman S. Blodgett, Worcester, Mass.

[22] Filed: Oct. 20, 1975

[21] Appl. No.: 623,736

Related U.S. Application Data

[63] Continuation of Ser. No. 510,448, Sept. 30, 1974, abandoned.

[52] U.S. Cl. .............................. 128/90; 128/89 R; 264/222
[51] Int. Cl.² ......................................... A61F 5/04
[58] Field of Search .................... 128/90, 89, 87; 264/222

[56] References Cited

UNITED STATES PATENTS

| | | |
|---|---|---|
| 3,692,023 | 9/1972 | Phillips et al. .................... 128/90 |
| 3,809,600 | 5/1974 | Larson ................................. 128/90 |
| 3,853,124 | 12/1974 | Larson ................................. 128/90 |
| 3,906,943 | 9/1975 | Arluck ................................. 128/90 |

*Primary Examiner*—John D. Yasko
*Attorney, Agent, or Firm*—Norman S. Blodgett; Gerry A. Blodgett

[57] ABSTRACT

An orthopedic cast made of a thermoplastic polyester having a melting point between 40° C and 70° C, particularly poly(epsilon-caprolactone) having a weight average molecular weight of over 30,000. The cast is formed of a continuous or foraminous sheet which is either solid polyester or polyester on a substrate which is not melted at the melting point of the polyester. The sheet is made plastic by heating in water of suitable temperature and then wrapping around the subject limb.

3 Claims, 4 Drawing Figures

METHOD OF FORMING AN ORTHOPEDIC CAST

This is a continuation, of application Ser. No. 510,448 filed Sept. 30, 1974.

BACKGROUND OF THE INVENTION

It has long been an objective of orthopedic surgeons to find a better method of immobilizing limbs than the use of casts made from plaster. Several schemes based on the use of high polymeric or plastic materials have been devised and several of these are in use. The plastics used are usually applied in a liquid or semi-liquid state and then post-cured to a rigid structure by ultraviolet light, heat, catalysts or other techniques which are well-known in the art of curing of plastic materials.

These methods have found a certain amount of acceptance but they suffer from some drawbacks. The curing reaction is not fast and the equipment which must be used is in many cases cumbersome. These disadvantages are sufficiently serious that plaster is still by far the most usual material used in orthopedic work.

Little attention has been given to the use of thermoplastic high polymers as a cast material. Consideration of the properties of thermoplastics indicates they have one major advantage over the materials heretofore employed. They do not require post-curing. They simply harden on cooling. However, there is no obvious method for applying thermoplastics in orthopedics. Most thermoplastics melt at quite a high temperature and the patient could never tolerate the heat necessary to form the material while directly in contact with or closely adjacent to the skin. Also, there is no simple method for forming a thermoplastic into the shape necessary to conform closely to the configuration required to confine closely the damaged limb or portion of the body to be immobilized.

The thermoplastic cast materials thus far developed suffer from various deficiencies which hinder widespread acceptance. Often the melting point is too high and hardening rate too fast to allow direct forming of the cast on the patient's limb. Melting of the cast material often requires ovens and other cumbersome equipment. Some materials either do not stick to themselves or require careful surface preparation. Some materials do not store well. Often a material which has a low melting point is not sufficiently rigid at temperatures to which the cast will be exposed. These and other difficulties experienced with the prior art devices have been obviated in a novel manner by the present invention.

It is, therefore, an outstanding object of the invention to provide an orthopedic cast which is clean and simple to apply.

Another object of this invention is the provision of an orthopedic cast which can be applied in a short time.

A further object of the present invention is the provision of an orthopedic cast which is light, strong, and sanitary in use, which allows circulation of air under the cast, and which permits washing of the limb.

It is another object of the instant invention to provide an orthopedic cast which does not require cumbersome equipment to apply.

A still further object of the invention is the provision of an orthopedic cast which reliably adhers to itself during application.

It is a further object of the invention to provide an orthopedic cast which can be applied to the patient while the cast is still in a plastic state.

It is a still further object of the present invention to provide an orthopedic cast which can be pre-formed and which will maintain the pre-formed shape even when rendered plastic.

With these and other objects in view, as will be apparent to those skilled in the art, the invention resides in the combination of parts set forth in the specification and covered by the claims appended hereto.

SUMMARY OF THE INVENTION

This invention involves an orthopedic cast system in which a cast is formed by wrapping a sheet of thermoplastic polyester which has been brought to its melting point of 50° C to 70° C around the subject limb and allowing the sheet to cool to hardness. The sheet is preferably heated in water and bonds to itself while molten. The sheet is preferably formed of polyester on a substrate which is solid at the melting point of the polyester. The preferred polyester is poly(epsilon-caprolactone) having a weight-averaged molecular weight of over 30,000.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
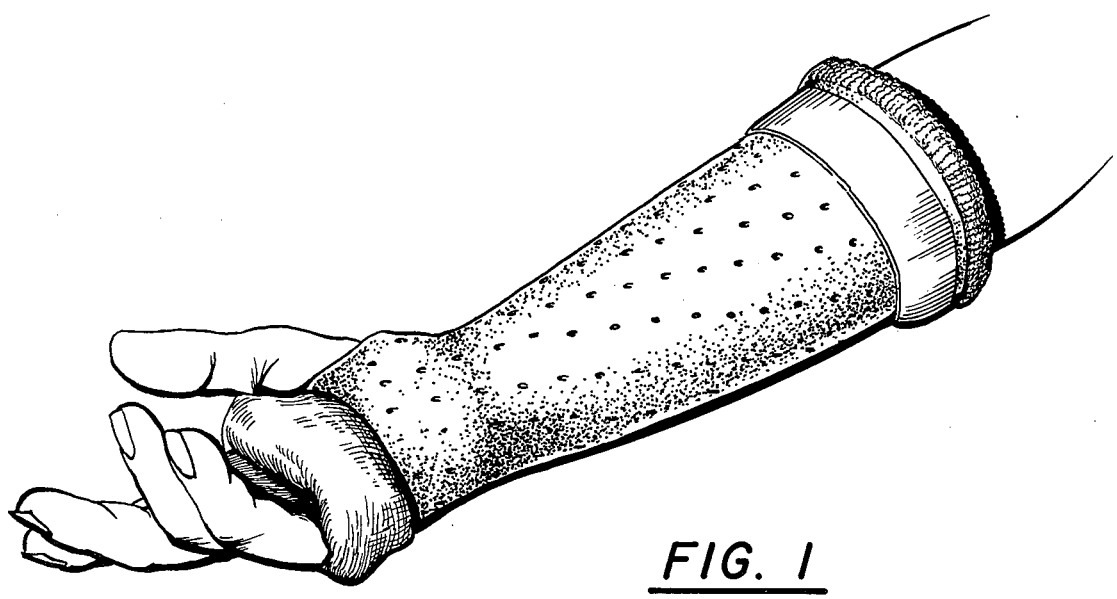
FIG. 1 is a perspective view of a wrist cast embodying the principles of the present invention in use on a human limb.

It is first necessary that if a thermoplastic is to be used as a cast material it should soften at a sufficiently low temperature that it can be formed directly on the patient without injury due to scalding or burning. There are quite a few high polymers which melt or soften at temperatures ranging from 40° C to 70° C, temperatures which conceivably could be used for forming the material without causing skin damage. Among the materials which melt in the correct range are poly(ethylene adipate), poly(epsilon-caprolactone), polyvinyl stearate, cellulose acetate butyrate, and ethyl cellulose. The first three materials mentioned exhibit true crystalline melting in this temperature range. In the case of cellulose acetate butyrate and ethyl cellulose the phenomenon noted is the so-called glass transition temperature. Poly(propylene oxide) has a crystalline melting temperature of 74° C. This temperature is a little high to be considered for this use but, as is well known in the art, judicious addition of comonomers to the poly(propylene oxide) will yield a lower melting temperature.

Among the materials cited, one which is in commercial production is poly(epsilon-caprolactone). The properties given for this thermoplastic suggest it might be ideal for use in orthopedic casts. Most important, it is a crystalline polymer which melts at 60° C. At room temperature it is quite stiff with a 1% secant modulus of 50,000 psi at 23° C. The stiffness remains high as the temperature is raised. At 60° C some melting occurs and the stiffness modulus is 20,000 psi. A few degrees beyond 60° C the polymer is completely molten. Beyond the melting temperature the polymer is formable by conventional plastic processing techniques. Furthermore, the manufacturer claims it is non-toxic. A 15% solution in dimethyl phthalate was non-irritating to rabbit skin and eyes. Although the best weight average molecular weight is about 40,000, or above, and above 30,000 is preferred, material down to 15,000 is operable but brittle as a cast.

The question remains as to how the plastic can be formed into a cast by some simple means readily applicable in the orthopedic surgeons office or hospital. Plaques of poly(epsilon-caprolactone) about ⅛ inch thick can be heated gently in an oven to a temperature slightly above the melting temperature. Supported by a rigid plate underneath the specimen with a polyethylene film between the plate and the plaque, the melted plaque retains its original shape. The polyethylene film can be picked up and used to transfer the molten polymer to the limb or other object to be wrapped and immobilized. On cooling, the poly(epsilon-caprolactone) becomes rigid and the polyethylene film is readily pealed off.

This technique is somewhat cumbersome. It is not easy to make good seals at joining surfaces. Also, if the finger or skin comes in contact with the molten plastic, it sticks and a stringy mess difficult to remove from the hands ensues.

It was very surprising to find this difficulty can be readily obviated by simply melting the plaque in water at 60° C. The warm plaque appears to absorb a fair amount of moisture and, under these conditions, it shows no tendency to stick to the skin. The plaque can be removed from the water, wrapped around the limb, and formed by kneading into shape by hand. The molten plastic cools and within a minute it is very rigid. The seal at the lap of the opposite edges is strong. The molten plastic can be applied directly to the skin and only a slight feeling of warmth is noted.

One difficulty with this procedure has been noted. The plaque, on melting in the water, distorts in shape when it is lifted from the water unless great care is used. This problem is obviated by laminating the poly(epsilon-caprolactone) to a rigid structure which does not melt at 60° C. It is preferable to contain the rigidifying structure internally so that the polymer is on both outer surfaces. One method which has been used is to laminate two sheets of poly(epsilon-caprolactone) on either side of a piece of cheese cloth. This type structure does not distort and it retains sufficient flexibility so that it can be readily formed to the proper configuration when applied to the limb.

Sheets or plaques of poly(epsilon-caprolactone) containing the internal rigidizing structure can be made by several methods. For example, two films of poly(epsilon-caprolactone) previously formed by conventional processes can be run between rollers with the cloth or other rigidifying structure between them. The inner surfaces of the film can be heated by infrared heaters or the like to provide a melted condition for lamination.

Another potential method is to dip coat the cloth in a solution of the polymer. On drying the proper structure is obtained.

In either case it may be desirable to provide a porous structure so that the final cast is breathable and more comfortable for the wearer. If the lamination procedure is used, this can be done by a post-perforation step. In the case of the dip coating method breathability can be obtained by making the solution of the polymer sufficiently dilute so that the open pores of the cloth do not bridge with polymer.

In general it would not be expected that the orthopedic surgeon would be able to apply the entire cast from a single plaque. It will often be necessary to prepare the entire cast by adding section after section. The question arises as to whether a new section can be made to adhere tightly to a previously cooled section. It has been found that this can be done by first coating the cooled section in the area to which the next section is to come in contact with a solution of poly(epsilon-caprolactone) in a suitable solvent such as toluene.

EXAMPLE 1

Pellets of poly(caprolactone) designated PCL-700 (weight average molecular weight 30,000) from Union Carbine Corp. were formed by heating and pressing into a 1/16 inch sheet, 3 inches × 3 inches. The sheet was immersed in water at 60° C until the cloudiness due to crystallinity disappeared. This takes about 40 seconds. The sheet was removed from the water and wrapped around the index finger. On cooling, a rigid structure suitable for an orthopedic cast resulted.

EXAMPLE 2

Since some distortion of the sheet took place when it was removed from the water, a second 3 inches × 3 inches plaque was made. This time a piece of two-mil. polyethylene film was laminated to one surface during the pressing operation. Much better dimensional stability resulted. However, forming the lap seal at the two opposing edges was somewhat difficult because of the polyethylene. On cooling, the polyethylene peeled off with no difficulty.

EXAMPLE 3

Figure 3:
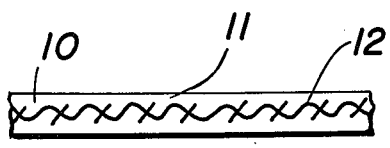
FIG. 3 is a cross-sectional view of a continuous composite sheet.

In this experiment two separate plaques were first made. A piece of cheesecloth 12 was interposed between the plaques 11 as shown in FIG. 3 and lamination carried out by remolding. The molten piece has good dimensional stability and, when wrapped around a ¾ inch diameter rod, the lap seal formed was very strong. Applying proper pressure with the fingers at the lap seal is sufficient to form a smooth seal, with the edge of the overlapped piece forming a barely noticeable line on the surface of the finished cast.

EXAMPLE 4

Figure 4:
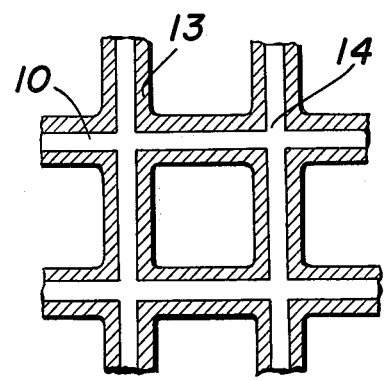
FIG. 4 is a cross-sectional view of a foraminous, composite sheet.

A solution of 60 g. PCL-700 in 200 ml. toluene was made. A 12 mesh glass cloth 14 made from glass fibres was coated with this solution by dipping and allowing to air dry followed by heating. The strands of the cloth are surrounded by a coating 13 as shown in FIG. 4, but the pores of the glass cloth remained open. The cloth was dipped in water at 60° C and wrapped around a mandrel with considerable overlap of successive layers. A rigid structure suitable for an orthopedic cast was formed.

EXAMPLE 5

The experiment of Example 4 was repeated this time using a glass cloth made from filament glass. The results were similar to those obtained in Example 4.

EXAMPLE 6

Several plaques of the type described in Example 3 were made. One plaque was formed around a mandrel as previously described and allowed to cool thoroughly.

The section to which a second plaque was to be attached was then coated with a 15% solution of poly(epsilon-caprolactone) in toluene. A minute or so later, a second plaque heated in water at 60° C was attached to the first. On cooling, the seal was very strong and could not be broken by hand.

EXAMPLE 7

A sample of Vexar plastic netting designated 25 CDS 89 was obtained from DuPont. This code designation stands for a strand diameter of 25 mils., made from low density polyethylene, in diamond pattern, sheet form, 8 strands per inch, with a 90° angle between intersecting strands. The netting was laminated by hot pressing between two sheets of poly(epsilon-caprolactone), PCL-700 from Union Carbide. The thickness of the laminate structure obtained was 1/16 inch.

A piece of the laminate was placed over the open end of a hemispherical cup, about 2 inches in diameter with vent holes at the bottom to allow escape of air. The laminate was heated with a hot-air gun until it started to sag. At this time a second hemispherical cup was positioned with the spherical end on the molten plastic and then forced into the first hemisphere. After cooling, the hemispheres were removed leaving the treated part of the laminate in hemispherical form. Observation of the formed piece showed the interior netting structure had distorted to conform to the new shape. This experiment shows the laminate can be formed by conventional molding, vacuum forming or other techniques to give objects of desired shapes.

EXAMPLE 8

A piece of the laminate from Example 7 about 1 inch wide by 5 inches long was formed into a U-shape by draping it over a 2 inch diameter mandrel and heating with a heat gun to a temperature high enough to bring the interior polyethylene netting into molten form. The U-shaped piece was heated in water at 65° C. The U-shape was retained in the water. While in the water, the ends of the U were distorted manually by either forcing the ends closer together or further apart. On release, the U-shape came back to its original contour.

This example demonstrates that a laminate of this type post-formed or molded at a temperature sufficient to melt the netting plastic, will retain its shape when reheated in 65° C water.

EXAMPLE 9

Figure 2:
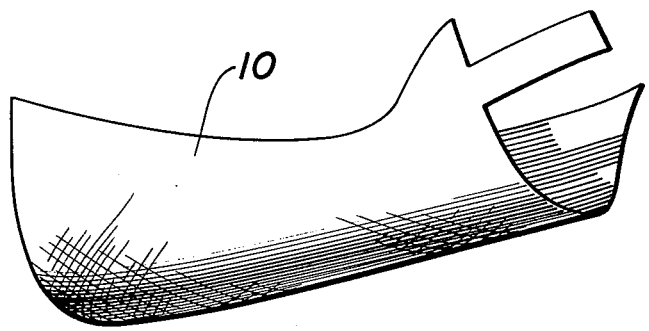
FIG. 2 is a perspective view of a pre-formed cast ready for heating and application.

A laminate structure of the type described in Example 1 in the form of a flat sheet 10 inches long by 6 inches wide was draped over a tapered mandrel with the length parallel to the mandrel. The diameter of the mandrel varied from 2 inches at one end to 2 ¾ inches at the other. It was heated as previously described forming a U-shape when observed from either end. Two small sections were cut from the 2 inches diameter end to form a structure as shown in FIG. 2.

This type structure is suitable for immobilizing the wrist and forearm as shown in FIG. 1. The piece is heated in water at about 65° C, removed, placed over the forearm, the longitudinal edges brought together in a lap seal, and the flag folded between the thumb and index finger, the end of the flag lap-sealed to the main part of the cast just below the thumb.

EXAMPLE 10

A laminate structure was made from Vexar plastic netting 20PDT 46 tubing, cut and opened to form a flat sheet, and applying the methods previously described. 20PDT 46 designates a strand diameter of 20 mils., made from polypropylene, in diamond pattern, tube form, 4 strands per inch and 60° angle between strands. This laminate could be formed into various shapes as described in previous examples except that higher temperatures had to be employed because of the higher melting temperature of polypropylene.

EXAMPLE 11

Another matter is how to handle the situation where one wishes to immobilize the arm in a position when the forearm and the upper arm are at right angles to one another. The construction suggested can be used to do this but it might be somewhat difficult requiring a patchwork application of several pieces of the polyester plastic.

Here the cast material was pre-formed into sort of a boat shape, or a section of a toroid. Naturally, it would be difficult to pre-form the cast material to this shape if the material used inside the cast to maintain dimensional stability is not readily formable like the cheesecloth previously used. However, one might use something formable like a higher melting polymer in cloth or perforated form as the inside of the cast material. The poly(epsilon-caprolactone) is first extruded or otherwise applied to the surfaces of the cloth or perforated plastic. Then the flat sheet resulting is heated to a temperature above that needed to melt the interior structure. The sheet is then molded into a boat form by vacuum forming or some other technique.

A structure of this type can be heated in water as previously described. The interior structure will not melt and dimensional stability will be maintained. The elbow is inserted into the boat and the cast material manually formed around the contour of the arm.

Another advantage may accrue if the interior cloth is made from either polypropylene or polyethylene. Both are lower in density than water while the poly(epsilon-caprolactone) is higher in density. Thus, the entire structure can be made to match the density of the hot water and this will facilitate handling in the water with less tendency to distort or stick to the bottom of the container.

EXAMPLE 12

Vexar plastic netting designated 20 PDT 86, 20 mil. strands, polypropylene, 8 strands to the inch, was cut into strips 1 ½ inches wide by 3 feet long. A solution of poly(epsilon-caprolactone) in toluene at a concentration of 15% PCL-700 in the solution was made. The netting strip was then dip coated by passing it through the solution and allowed to dry. After drying, the strip was wound into a tight cylinder and maintained in this shape by means of a rubber band. The cylinder was then heated in water at 65° C for 5 minutes. The cylinder was then removed from the water and the rubber band taken off. The cylinder was then removed from the water and the rubber band taken off. The cylinder was then unwound and simultaneously wound around a 2 inches mandrel in the shape of a spiral. The cylinder was easily unwound. The spiral on the mandrel, after cooling, formed a strong bond between successive layers.

It is obvious that minor changes may be made in the form and construction of the invention without departing from the material spirit thereof. It is not, however, desired to confine the invention to the exact form herein shown and described, but it is desired to include all such as properly come with the scope claimed.

The invention having been thus described, what is claimed as new and desired to secure by Letters Patent is:

1. A method of forming an orthopedic cast, comprising the steps of:

a. forming a flat sheet of a primary polymer in the form of poly (epsilon-caprolactone) having a melting point of between 50° C and 75° C and a half-time of crystallization at body temperature greater than 1 minute but less than 20 minutes, wherein the primary polymer is coated on a substrate, the substrate being a solid at the melting point of the primary polymer, the substrate being formed of an open weave netting of a secondary polymer, which secondary polymer is capable of being thermoformed by viscous flow at temperatures between 90° C and 170° C, b. heating the sheet to the thermoforming temperature of the substrate a secondary polymer, molding the sheet to a preform contour suitable for conforming to a portion of the body and, immobilizing the pre-form by cooling, c. subsequently heating the pre-form to a temperature above the softening point of the primary polymer but below the thermoforming temperature of the secondary polymer by immersing the pre-form in water at a suitable temperature, d. applying the pre-form to the portion of the body to be immobilized, and e. allowing the sheet to cool to body temperature.

2. A method as recited in claim 1, wherein the primary polymer has a formula

$$\{O-(CH_2)_5-CO\}_x$$

where $x$ makes the weight average molecular weight greater than 30,000.

3. A method as recited in claim 1, wherein two edges of the sheet are contacted during a step (d) and held together as the sheet cools.

* * * * *